United States Patent
Matsuo et al.

(10) Patent No.: US 9,638,603 B2
(45) Date of Patent: May 2, 2017

(54) INSPECTING DEVICE, DRAWING DEVICE AND INSPECTING METHOD

(71) Applicant: SCREEN Holdings Co., Ltd., Kyoto (JP)

(72) Inventors: Kiyotaka Matsuo, Kyoto (JP); Yuichi Hanada, Kyoto (JP)

(73) Assignee: SCREEN Holdings Co., Ltd., Kyoto (JP)

( * ) Notice: Subject to any disclaimer, the term of this patent is extended or adjusted under 35 U.S.C. 154(b) by 0 days.

(21) Appl. No.: 15/003,907

(22) Filed: Jan. 22, 2016

(65) Prior Publication Data

US 2016/0223428 A1   Aug. 4, 2016

(30) Foreign Application Priority Data

Jan. 29, 2015 (JP) ................. 2015-015046

(51) Int. Cl.
    *G01N 21/00* (2006.01)
    *G01M 11/00* (2006.01)

(52) U.S. Cl.
    CPC ................... *G01M 11/005* (2013.01)

(58) Field of Classification Search
    CPC ............. G01M 11/005; G01N 21/9501; G01N 21/956; G01N 21/95
    USPC ........... 356/213–226, 124–127, 237.1–237.5
    See application file for complete search history.

(56) References Cited

U.S. PATENT DOCUMENTS

| 5,617,203 A * | 4/1997 | Kobayashi ....... G01N 21/95623 250/550 |
| 2014/0320835 A1* | 10/2014 | Fujiwara ................ G02B 26/06 355/67 |

FOREIGN PATENT DOCUMENTS

JP    2014-106513    6/2014

* cited by examiner

*Primary Examiner* — Hoa Pham
(74) *Attorney, Agent, or Firm* — Ostrolenk Faber LLP

(57) ABSTRACT

A spatial modulator is configured by arranging a plurality of modulating units in an X-axis direction, the modulating units each including at least one light modulating element having a fixed reflecting surface with a constant height from a base surface and a movable reflecting surface with a variable height from the base surface. The spatial modulator spatially modulates a laser beam by the plurality of modulating units. A driver circuit unit applies a voltage corresponding to a driving value to each of the plurality of modulating units, to drive the modulating units individually. A shift amount acquiring portion acquires a driving value at a reference time point and a driving value at an inspecting time point which correspond to a specific light amount value, and acquires a differential value thereof as a shift amount.

15 Claims, 10 Drawing Sheets

F I G. 7
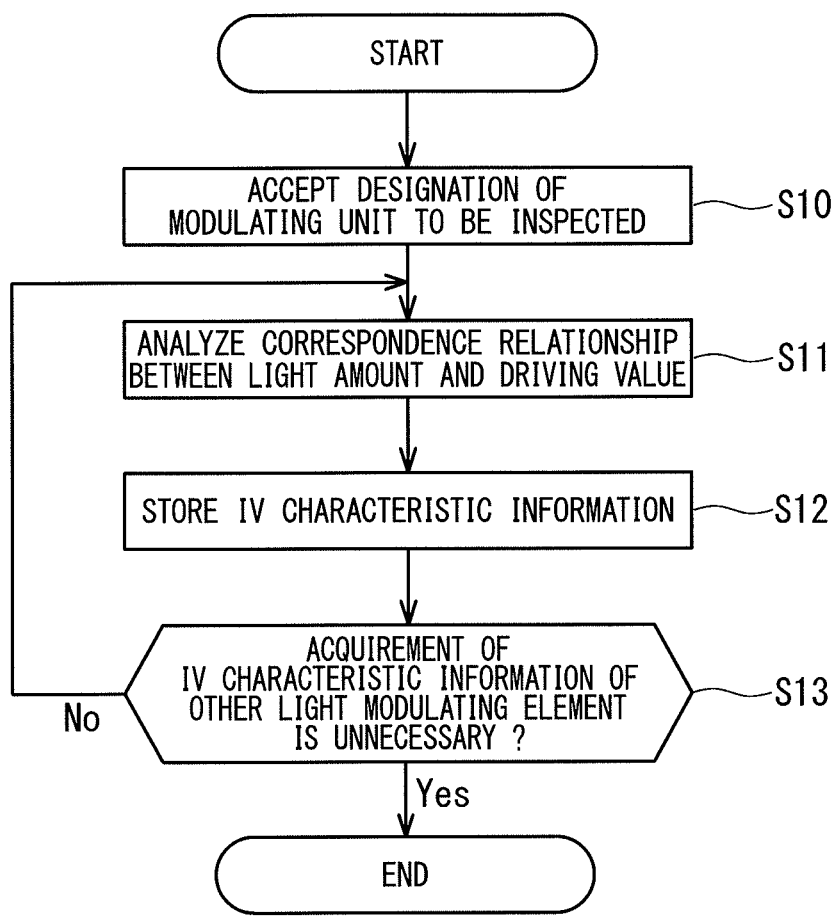

F I G. 1 2
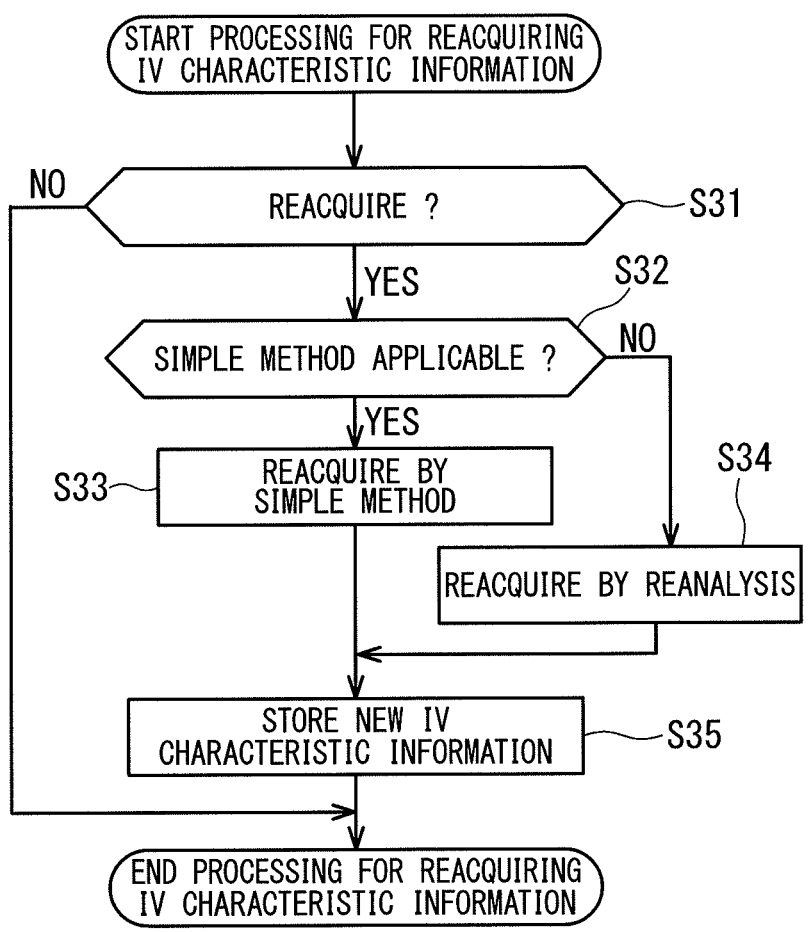

INSPECTING DEVICE, DRAWING DEVICE AND INSPECTING METHOD

BACKGROUND OF THE INVENTION

Field of the Invention

The present invention relates to a technique for inspecting a spatial light modulator.

Description of the Background Art

A GLV (Grating Light Valve) (registered trademark of Silicon Light Machines (San Jose, Calif.)) which is a ribbon diffracting element is known as a spatial light modulator. Referring to the GLV, a modulating element is formed by a fixed reflecting surface and a movable reflecting surface with respect to a fixed surface, and a plurality of modulating units are arranged in a predetermined direction. In the case where the GLV is used, uniformity of light reflected from the GLV greatly affects an exposure result. For this reason, in a drawing device using the GLV, it is indispensable to adjust an amount of light reflected from the GLV. In recent drawing devices, particularly, an enhancement in fineness of drawing is required and an enhancement in fineness of adjustment of the amount of reflected light is also demanded.

Referring to the GLV, a voltage is applied to a movable ribbon configuring the movable reflecting surface in each modulating unit so that the movable reflecting surface is moved to a recessed position with respect to the fixed reflecting surface. A size of the recessed part can be regulated depending on an amount of the voltage to be applied, and light incident on each modulating unit is switched into zero order light and diffracted light in order other than zero order so that the amount of the light reflected from the modulating unit can be controlled. When the GLV is attached to the drawing device, a relationship (hereinafter referred to as an "IV characteristic") between an amount of reflected light (I) and an amount of a voltage (V) is analyzed for each modulating unit. Based on a result of the analysis, the amount of the light reflected from each modulating unit is controlled.

The related art relating to the present invention is described in Japanese Patent Application Laid-Open No. 2014-106513, for example.

In general, a great load is applied to the GLV because a high power laser beam is radiated thereon. For this reason, it is known that each modulating unit is deteriorated with an increase in an operating time of the GLV and the amount of the reflected light fluctuates with respect to an equal voltage. Therefore, it is necessary to periodically reacquire IV characteristic information of the modulating unit. However, respective modulating units have different characteristics from each other, and furthermore, times required for exposure to the laser beam are also different from each other. For this reason, the IV characteristic information should be acquired for each modulating unit. In the case where the number of the modulating units is large, accordingly, a labor and time is greatly required for reacquiring the IV characteristic information.

Moreover, there is no effective index for quantitatively grasping a degree of deterioration from an initial state for each modulating unit of the GLV. For this reason, it is hard to grasp which modulating unit is deteriorated or to what degree the modulating unit is deteriorated.

SUMMARY OF THE INVENTION

The present invention is directed to an inspecting device for inspecting a spatial light modulator to modulate a light amount while reflecting an incident laser beam for every plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from the base surface.

The inspecting device according to a first aspect includes a modulator driving portion for applying a voltage corresponding to a driving value to each of the plurality of modulating units to drive the movable ribbon, to control a light amount of a laser beam output by the modulating unit, a light amount detector for detecting the light amount of the laser beam reflected by each of the plurality of modulating units, a storing portion for storing information indicative of a first driving value corresponding to a first light amount for one of the plurality of modulating units or for every two or more of the modulating units, and a shift amount acquiring portion for acquiring a second driving value corresponding to an output of the first light amount again, to acquire a differential value between the first driving value and the second driving value as a shift amount for one of the plurality of modulating units or for every two or more of the modulating units.

According to the first aspect, deterioration in each of the modulating units in the spatial light modulator can be inspected based on the shift amount of the driving value corresponding to an identical light amount (the first light amount). Therefore, a degree of the deterioration in the modulating unit can be grasped for each modulating unit.

A second aspect is directed to the inspecting device according to the first aspect in which the storing portion stores information indicative of a correspondence relationship between a light amount and a driving value for one of the plurality of modulating units or for every two or more of the modulating units, the information being first IV characteristic information in which a driving value corresponding to the output of the first light amount is set to be the first driving value, and the inspecting device further includes an IV characteristic information acquiring portion for changing a driving value corresponding to each light amount indicated by the first IV characteristic information by an amount corresponding to the shift amount, to acquire second IV characteristic information for one of the plurality of modulating units or for every two or more of the modulating units.

According to the second aspect, each driving value corresponding to each light amount indicated by the first IV characteristic information is changed by the amount corresponding to the shift amount so that the new second IV characteristic information is simply acquired. Therefore, a labor and time can be reduced more greatly as compared with the case where the correspondence relationship between the light amount and the driving value is reanalyzed.

A third aspect is directed to the inspecting device according to the second aspect in which the first IV characteristic information is information indicative of a first IV curve representing a correspondence relationship between a driving value and a light amount on two-dimensional coordinates constituted by an axis of the driving value and an axis of the light amount, and the IV characteristic information acquiring portion acquires, as the second IV characteristic information, a second IV curve obtained by moving the first IV curve by an amount corresponding to the shift amount along the axis of the driving value.

According to the third aspect, it is possible to simply acquire the IV curve representing the IV characteristic of each modulating unit after deterioration.

A fourth aspect is directed to the inspecting device according to the second or third aspect in which the storing portion stores, as shift amount history information, the shift amount which has been acquired by the shift amount acquiring portion for one of the plurality of modulating units or for every two or more of the modulating units, and the IV characteristic information acquiring portion determines necessity of acquirement of the second IV characteristic information based on an accumulated shift amount in which the shift amount recorded in the shift amount history information is accumulated.

According to the fourth aspect, it is possible to quantitatively grasp a degree of deterioration from a certain time point of a corresponding modulating unit by acquiring the accumulated shift amount. Accordingly, it is possible to suitably determine whether the second IV characteristic information should be acquired simply depending on the magnitude of the accumulated shift amount or whether the IV characteristic information should be acquired by reanalysis of the correspondence relationship between the light amount and the driving value.

A fifth aspect is directed to the inspecting device according to any one of the first to fourth aspects, in which the shift amount acquiring portion acquires the second driving value corresponding to the first light amount based on a relationship between a plurality of driving values included in a range from the first driving value to a third driving value and a light amount corresponding to each of the plurality of driving values.

According to the fifth aspect, the light amount is measured for each of a plurality of driving values included between the first driving value and the third driving value. Consequently, it is possible to specify the second driving value shifted from the first driving value.

A sixth aspect is directed to the inspecting device according to any one of the first to fifth aspects, in which the inspecting device further includes an inspecting portion for performing an inspection for one of the plurality of modulating units or for every two or more of the modulating units, the storing portion stores, as shift amount history information, the shift amount which has been acquired by the shift amount acquiring portion for one of the plurality of modulating units or for every two or more of the modulating units, and the inspecting portion inspects the modulating unit based on the shift amount history information.

According to the sixth aspect, it is possible to grasp a degree of deterioration for each modulating unit based on the shift amount history information in which the shift amount that has been acquired for each modulating unit is recorded.

A seventh aspect is directed to the inspecting device according to the sixth aspect, in which the inspecting portion performs an inspection for comparing an accumulated shift amount in which the shift amount recorded in the shift amount history information is accumulated with a prescribed threshold indicative of a life of the modulating unit.

According to the seventh aspect, it is possible to quantitatively grasp whether or not a service life is reached for each modulating unit based on the accumulated shift amount.

Moreover, an eighth aspect is directed to a drawing device for drawing a pattern on a substrate, the drawing device including a spatial light modulator for modulating a light amount while reflecting an incident laser beam for every plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from the base surface, a modulator driving portion for applying a voltage corresponding to a driving value to each of the modulating units to drive the movable ribbon, to control a light amount of a laser beam output by the modulating unit, a light amount detector for detecting the light amount of the laser beam reflected by each of the plurality of modulating units, a storing portion for storing information indicative of a first driving value corresponding to a first light amount for one of the plurality of modulating units or for every two or more of the modulating units, and a shift amount acquiring portion for acquiring a second driving value corresponding to an output of the first light amount again, to acquire a differential value between the first driving value and the second driving value as a shift amount for one of the plurality of modulating units or for every two or more of the modulating units.

Furthermore, a ninth aspect is directed to a method of inspecting a spatial light modulator for modulating a light amount while reflecting an incident laser beam by application of a voltage corresponding to a driving value from a modulator driving portion through each of a plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from the base surface, the method including the steps of (a) acquiring a first driving value corresponding to a first light amount of the laser beam reflected by the modulating unit for one of the plurality of modulating units or for every two or more of the modulating units, (b) acquiring a second driving value corresponding to the first light amount again for one of the plurality of modulating units or for every two or more of the modulating units, and (c) acquiring a differential value between the first driving value and the second driving value as a shift amount.

Therefore, it is an object of the present invention to provide a technique for suitably acquiring IV characteristic information of each modulating unit in a spatial light modulator or appropriately inspecting deterioration in each modulating unit.

These and other objects, features, aspects and advantages of the present invention will become more apparent from the following detailed description of the present invention when taken in conjunction with the accompanying drawings.

BRIEF DESCRIPTION OF THE DRAWING

FIG. 7 is a flowchart showing a flow of processing for acquiring IV characteristic information of a spatial light modulator which is to be executed in the drawing device according to the preferred embodiment;

FIG. 12 is a flowchart showing a detailed flow of processing for reacquiring the IV characteristic information.

DESCRIPTION OF THE PREFERRED EMBODIMENTS

<1. Whole Structure of Drawing Device 1>

Figure 1:
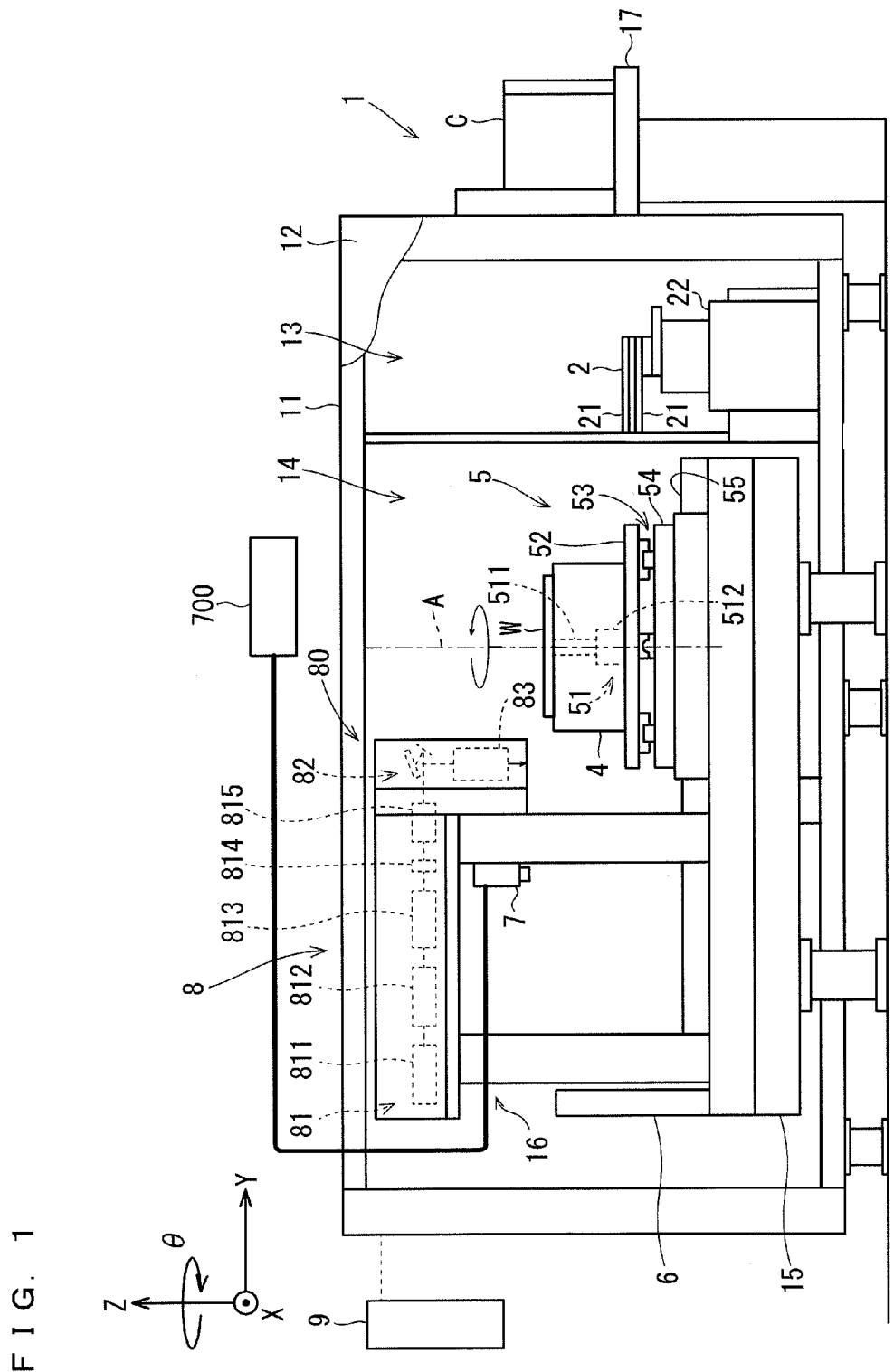
FIG. 1 is a side view schematically showing a structure of a drawing device according to a preferred embodiment.
Figure 2:
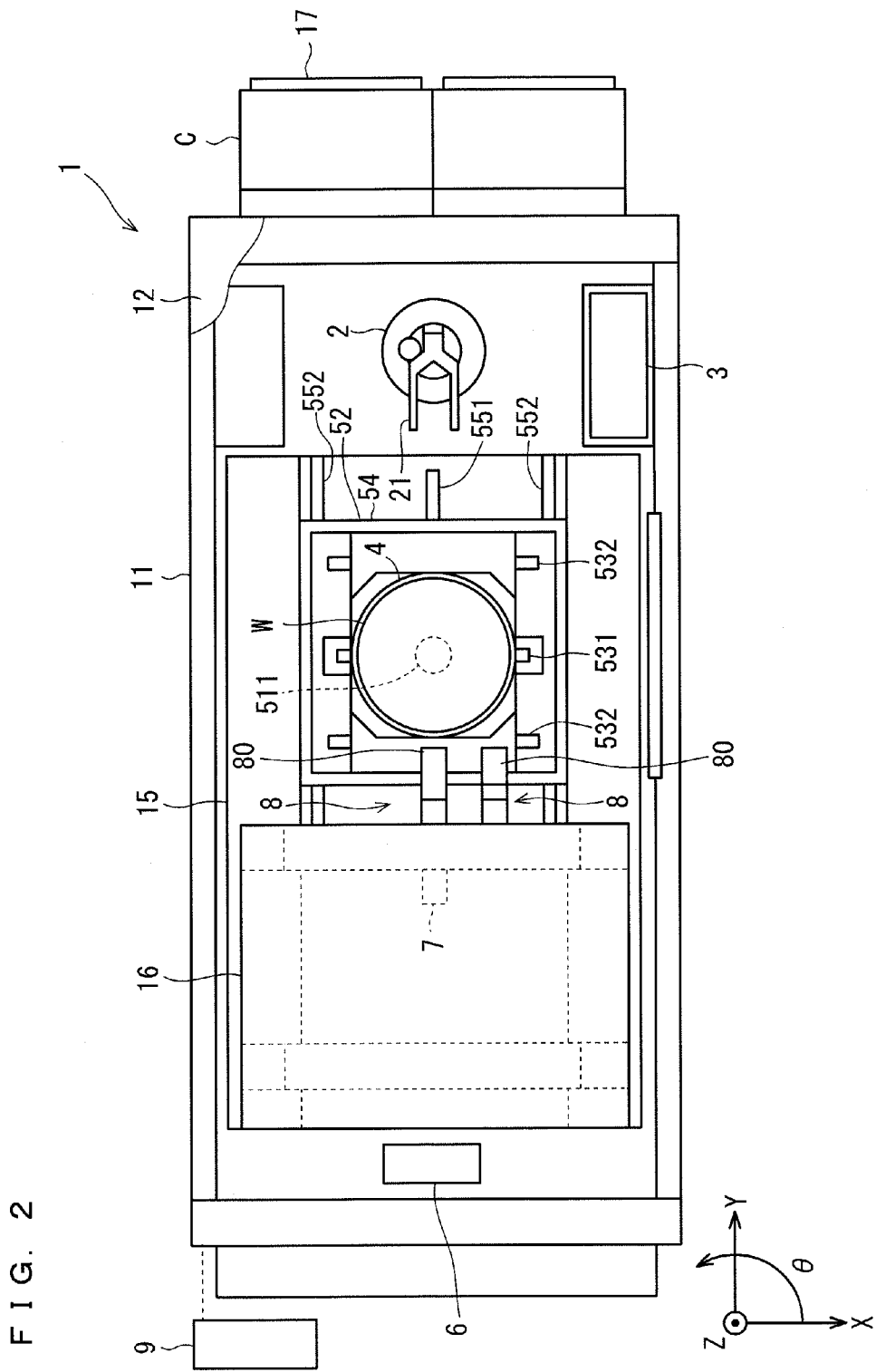
FIG. 2 is a plan view schematically showing the structure of the drawing device according to the preferred embodiment.

FIG. 1 is a side view schematically showing a structure of a drawing device 1 according to a preferred embodiment. FIG. 2 is a plan view schematically showing the structure of the drawing device 1 according to the preferred embodiment. In FIGS. 1 and 2, for convenience of description, a part of a cover panel 12 is not shown.

The drawing device 1 serves to radiate light (drawing light) modulated spatially depending on CAD data or the like onto an upper surface of a substrate W on which a layer made of a photosensitive material such as a resist is formed, thereby exposing (drawing) a pattern (for example, a circuit pattern). For example, the substrate W to be processed in the drawing device 1 includes a semiconductor substrate, a printed wiring board, a substrate for a color filter provided in a liquid crystal display or the like, a glass substrate for a flat panel display provided in a liquid crystal display, a plasma display device or the like, a substrate for a magnetic disk, a substrate for an optical disk, a panel for a solar cell and the like. In the following description, it is assumed that the substrate W is a circular semiconductor substrate.

The drawing device 1 has a structure in which the cover panel 12 is attached to a ceiling surface, a floor surface and a circumferential surface of a framework configured by a body frame 11. The body frame 11 and the cover panel 12 form a housing of the drawing device 1. An internal space of the housing of the drawing device 1 (that is, a space surrounded by the cover panel 12) is divided into a delivering region 13 and a processing region 14. A base 15 is disposed in the processing region 14. Moreover, a gate type support frame 16 is provided on the base 15.

The drawing device 1 includes a conveying device 2, a prealignment portion 3, a stage 4, a stage driving mechanism 5, a stage position measuring portion 6, a mark image pickup unit 7, an exposure unit 8 and a control portion 9. These components are disposed on an inside of the housing of the drawing device 1 (that is, the delivering region 13 and the processing region 14) or an outside of the housing (that is, a space on an outside of the body frame 11).

<Conveying Device 2>

The conveying device 2 conveys the substrate W. The conveying device 2 is disposed in the delivering region 13 and conveys the substrate W into/out of the processing region 14. The conveying device 2 specifically includes two hands 21 and 21 for supporting the substrate W and a hand driving mechanism 22 for independently moving the hands 21 and 21 (forward and backward movement and up and down movement), for example.

A cassette mounting portion 17 for mounting a cassette C is disposed in a position adjacent to the delivering region 13 at an outside of the housing of the drawing device 1. The conveying device 2 takes out an unprocessed substrate W accommodated in the cassette C mounted on the cassette mounting portion 17 and conveys the unprocessed substrate W into the processing region 14, and furthermore, conveys a processed substrate W from the processing region 14 and accommodates the processed substrate W into the cassette C. The delivery of the cassette C to the cassette mounting portion 17 is performed by an external conveying device (not shown).

<Prealignment Portion 3>

The prealignment portion 3 performs processing (prealignment processing) for roughly correcting a rotating position of the substrate W prior to mounting of the substrate W on the stage 4, which will be described below. The prealignment portion 3 can include, for example, a mounting table configured rotatably, a sensor for detecting a position of a notch portion (for example, a notch, an orientation flat or the like) formed on a part of an outer peripheral edge of the substrate W mounted on the mounting table, and a rotating mechanism for rotating the mounting table. In this case, the prealignment processing in the prealignment portion 3 is performed by first detecting the position of the notch portion of the substrate W mounted on the mounting table by the sensor and subsequently rotating the mounting table in such a manner that the position of the notch portion is set to be a determined position by the rotating mechanism.

<Stage 4>

The stage 4 is a holding portion for holding the substrate W in the housing. The stage 4 is disposed on the base 15 provided in the processing region 14. The stage 4 specifically has a plate-like external shape, for example, and mounts and holds the substrate W on an upper surface thereof in a horizontal posture. A plurality of sucking holes (not shown) is formed on an upper surface of the stage 4 and a negative pressure (a sucking pressure) is formed on the sucking holes so that the substrate W mounted on the stage 4 is fixed and held on the upper surface of the stage 4.

<Stage Driving Mechanism 5>

The stage driving mechanism 5 moves the stage 4 with respect to the base 15. The stage driving mechanism 5 is disposed on the base 15 provided in the processing region 14.

Specifically, the stage driving mechanism 5 includes a rotating mechanism 51 for rotating the stage 4 in a rotating direction (a rotating direction around a Z axis (a θ-axis direction)), a support plate 52 for supporting the stage 4 through the rotating mechanism 51, and a sub scanning mechanism 53 for moving the support plate 52 in a sub scanning direction (an X-axis direction). The stage driving mechanism 5 further includes a base plate 54 for supporting the support plate 52 through the sub scanning mechanism 53 and a main scanning mechanism 55 for moving the base plate 54 in a main scanning direction (a Y-axis direction).

The rotating mechanism 51 rotates the stage 4 around a rotating axis A perpendicular to a mounting surface of the substrate W via a center of the upper surface (the mounting surface) of the stage 4. For example, the rotating mechanism 51 may have a structure including a rotating shaft portion 511 having an upper end fixed to a back face side of the mounting surface and extended along a vertical axis, and a rotation driving portion (for example, a rotating motor) 512 provided on a lower end of the rotating shaft portion 511 and rotating the rotating shaft portion 511. With this structure, the rotation driving portion 512 rotates the rotating shaft portion 511 so that the stage 4 is rotated around the rotating axis A in a horizontal plane.

The sub scanning mechanism 53 has a linear motor 531 configured by a mover attached to a lower surface of the support plate 52 and a stator provided on an upper surface of the base plate 54. Moreover, a pair of guide members 532 extended in the sub scanning direction is provided on the base plate 54, and a ball bearing capable of moving along each guide member 532 while sliding with respect to the guide member 532 is provided between the guide member 532 and the support plate 52. In other words, the support plate 52 is supported on the pair of guide members 532 through the ball bearing. With this structure, when the linear motor 531 is operated, the support plate 52 is moved smoothly in the sub scanning direction in a state where the support plate 52 is guided by the guide member 532.

The main scanning mechanism 55 has a linear motor 551 configured by a mover attached to a lower surface of the base plate 54 and a stator provided on the base 15. Moreover, a pair of guide members 552 extended in the main scanning direction is provided on the base 15, and an air bearing is provided between each guide member 552 and the base plate 54, for example. Air is usually supplied from utility equipment to the air bearing, and the base plate 54 is floated and supported in a noncontact manner on the guide member 552 by the air bearing. With this structure, when the linear motor 551 is operated, the base plate 54 is moved smoothly without friction in the main scanning direction in a state where the base plate 54 is guided by the guide member 552.

<Stage Position Measuring Portion 6>

The stage position measuring portion 6 measures a position of the stage 4. The stage position measuring portion 6 specifically emits a laser beam from the outside of the stage 4 toward the stage 4 and receives reflected light thereof, for example. The stage position measuring portion 6 configures an interference type laser length measuring device for measuring the position of the stage 4 (specifically, a Y position in the main scanning direction and a θ position in the rotating direction) based on an interference between the reflected light and the emitted light.

<Mark Image Pickup Unit 7>

The mark image pickup unit 7 is an optical device for picking up an image of the upper surface of the substrate W held on the stage 4. The mark image pickup unit 7 is supported on the support frame 16. Specifically, the mark image pickup unit 7 includes a barrel, a focusing lens, a CCD image sensor and a driving portion, for example. The barrel is connected, through a fiber cable or the like, to an illuminating unit 700 disposed on the outside of the housing of the drawing device 1 (that is, an illuminating unit for supplying illumination light for image pickup (light having such a wavelength as not to expose a resist on the substrate W or the like to light is selected as the illumination light). The CCD image sensor is configured by an area image sensor (a two-dimensional image sensor) or the like. Moreover, the driving portion is configured by a motor or the like and drives the focusing lens to change a height position thereof. The driving portion adjusts the height position of the focusing lens so that automatic focusing is performed.

In the mark image pickup unit 7 having such a structure, light emitted from the illuminating unit 700 is introduced into the barrel and is then guided to the upper surface of the substrate W on the stage 4 through the focusing lens. Thereafter, reflected light thereof is received by the CCD image sensor. Consequently, image pickup data on the upper surface of the substrate W is acquired. The image pickup data is transmitted to the control portion 9 and is used for the alignment (positioning) of the substrate W.

<Exposure Unit 8>

The exposure unit 8 is an optical device for forming drawing light. The drawing device 1 includes two exposure units 8. Naturally, the number of the exposure units 8 to be provided does not always need to be two but may be one or three or more.

The exposure unit 8 includes an exposure head 80 and a light source portion 81. The exposure head 80 includes a modulating unit 82 and a projecting optical system 83. The light source portion 81, the modulating unit 82 and the projecting optical system 83 are supported on the support frame 16. Specifically, the light source portion 81 is accommodated in a housing box mounted on a top plate of the support frame 16, for example. Moreover, the modulating unit 82 and the projecting optical system 83 are accommodated in the housing box fixed to a +Y side of the support frame 16.

Figure 3:
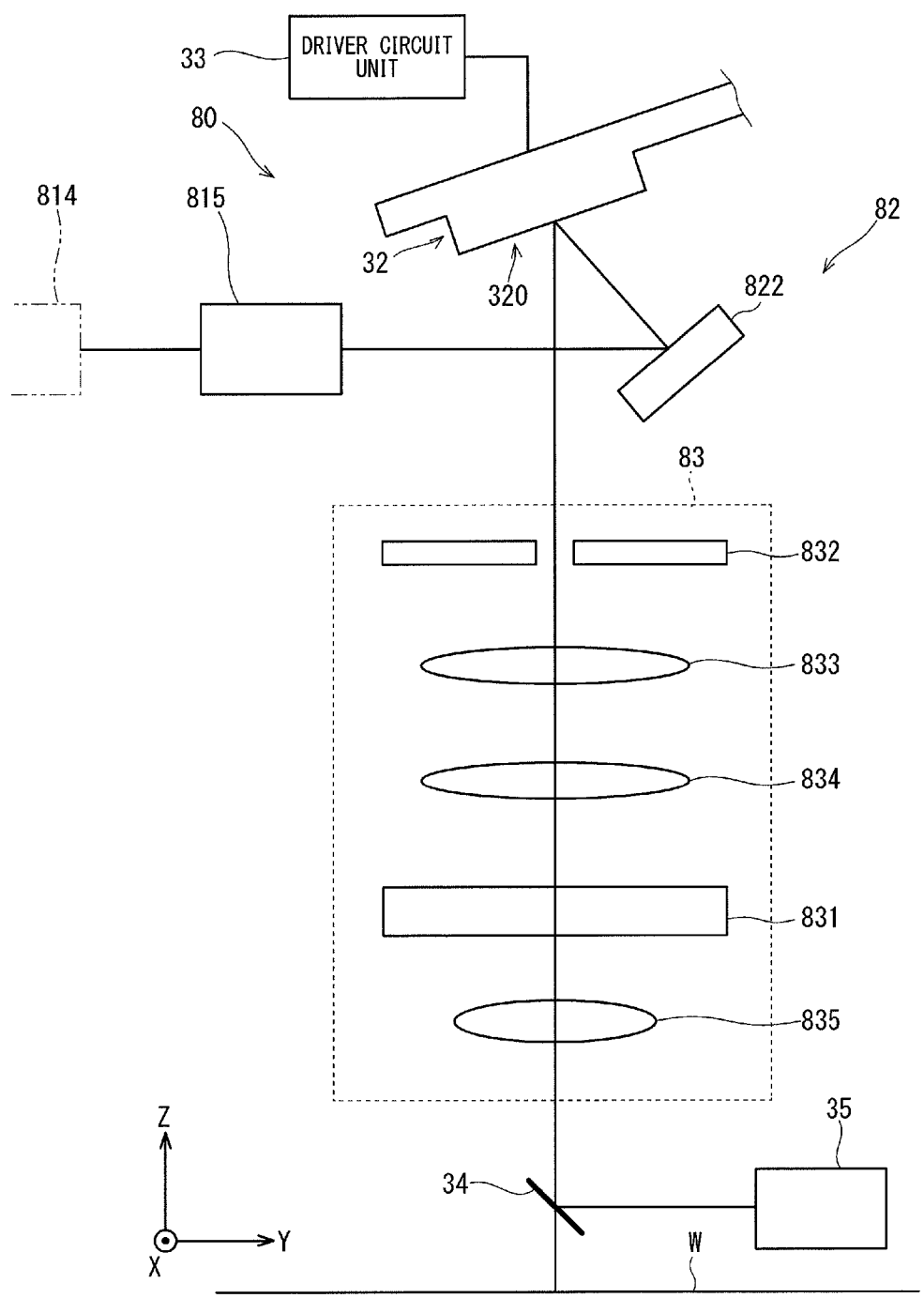
FIG. 3 is a view schematically showing an exposure head according to the preferred embodiment.

The light source portion 81, the modulating unit 82 and the projecting optical system 83 provided in the exposure unit 8 will be described with reference to FIG. 3 in addition to FIGS. 1 and 2. FIG. 3 is a view schematically showing the exposure head 80 according to the preferred embodiment.

a. Light Source Portion 81

The light source portion 81 emits light toward the exposure head 80. Specifically, the light source portion 81 includes a laser driving portion 811 and a laser oscillator 812 for emitting a laser beam from an output mirror (not shown) upon receipt of a driving operation from the laser driving portion 811, for example. Moreover, the light source portion 81 includes an illuminating optical system 813 for changing the light (a spot beam) emitted from the laser oscillator 812 into linear light having uniform intensity distribution (that is, a line beam as light having a band-shaped luminous flux section).

The light source portion 81 further includes a drawing focus lens 814 (a first lens) for converging the line beam emitted from the illuminating optical system 813 on a modulating surface 320 of a spatial light modulator 32. The drawing focus lens 814 is configured by a cylindrical lens, for example, and a cylindrical surface is disposed toward an upstream side of incident light. Moreover, the drawing focus lens 814 is disposed in such a height position that the line beam emitted from the illuminating optical system 813 is incident on a center line thereof (such a height position will be hereinafter referred to as a "reference position" of the drawing focus lens 814). However, a mechanism for changing the height position (the position in the Z direction) is provided on the drawing focus lens 814, and the drawing focus lens 814 is disposed in a position higher (or lower) than the reference position in some cases.

In the light source portion 81 having such a structure, a laser beam is emitted from the laser oscillator 812 upon receipt of the driving operation of the laser driving portion 811, and the laser beam is changed into a line beam in the illuminating optical system 813. The line beam emitted from the illuminating optical system 813 is incident on the drawing focus lens 814 and is emitted from the cylindrical surface, and is converged on the modulating surface 320 of the modulating unit 82. In other words, the modulating surface 320 serves as a light converging surface of the line beam.

Moreover, the light source portion 81 includes an attenuator 815. The attenuator 815 is provided on an optical path from the drawing focus lens 814 to the modulating unit 82 (see FIGS. 1 and 3). However, a position in which the attenuator 815 is to be provided is not limited thereto but can be provided in an appropriate position on the optical path from the laser oscillator 812 to the substrate W. The attenuator 815 reduces the light emitted from the light source portion 81 based on a control signal transmitted from the control portion 9. Consequently, the attenuator 815 changes, in a multistage, an amount of light emitted from the light source portion 81 toward the modulating unit 82.

b. Modulating Unit 82

The modulating unit 82 performs spatial modulation corresponding to pattern data over light incident thereon. However, "to spatially modulate light" implies that spatial distribution of light (an amplitude, a phase, a light polarization or the like) is changed. Moreover, the "pattern data" is data in which position information on the substrate W where light is to be irradiated is recorded in a pixel unit. The pattern data is received from an external terminal device connected through a network or the like, for example, or is read from a recording medium and is thus acquired, and is stored in a storage device 94 of the control portion 9 which will be described below.

The modulating unit 82 includes the spatial light modulator 32. The spatial light modulator 32 serves to reflect, in different directions from each other, necessary light for spatially modulating light by electrical control, for example, to contribute to pattern drawing and unnecessary light which is not caused to contribute to the pattern drawing. The spatial light modulator 32 includes a GLV (Grating Light Valve) to be a reflection type and diffraction grating type spatial light modulator.

Figure 4:
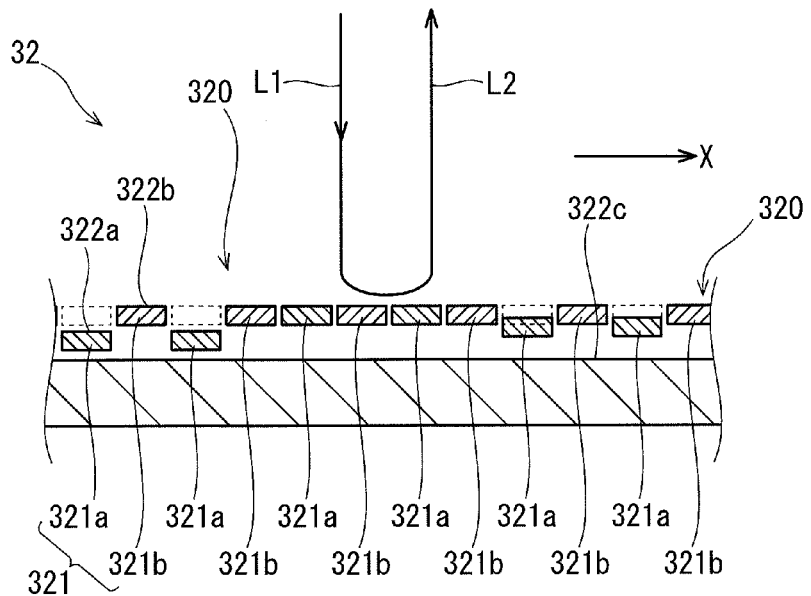
FIG. 4 is a schematic sectional view showing schematic sections of a plurality of light modulating elements on a perpendicular surface to a movable ribbon and a fixed ribbon.

FIG. 4 is a schematic sectional view showing schematic sections of a plurality of light modulating elements 321 on a perpendicular surface to a movable ribbon 321a and a fixed ribbon 321b. Each light modulating element 321 includes a single movable ribbon 321a and a single fixed ribbon 321a.

An upper surface of the movable ribbon 321 a and an upper surface of the fixed ribbon 321b include a movable reflecting surface 322a and a fixed reflecting surface 322b which are parallel with a base surface 322c in rear parts, respectively. The movable reflecting surface 322a and the fixed reflecting surface 322b are band-shaped and extended vertically in an array direction (herein, a parallel direction with the X-axis direction) of the light modulating element 321, respectively. In the spatial light modulator 32, the movable reflecting surface 322a and the fixed reflecting surface 322b are arranged alternately in the element array direction.

The movable ribbon 321 a can be moved upward and downward with respect to the base surface 322c and a height of the movable reflecting surface 322a from the base surface 322c is variable. The fixed ribbon 321b is fixed to the base surface 322c and a height of the fixed reflecting surface 322b from the base surface 322c is also fixed. Surfaces of the movable ribbon 321a and the fixed ribbon 321b are coated to reflect incident light L1.

The spatial light modulator 32 has a predetermined number of light modulating elements 321 forming a single modulating unit and has a structure in which a plurality of modulating units are arranged one-dimensionally in the X-axis direction. The spatial light modulator 32 is connected to a driver circuit unit 33 (a modulator driving portion) capable of individually applying a voltage to each of the plurality of light modulating elements 321. The driver circuit unit 33 can individually apply a voltage corresponding to a driving value to each of the movable ribbons 321a of the plurality of light modulating elements 321. The voltage is applied to the light modulating element 321 so that the movable ribbon 321a is flexed to be recessed with respect to the fixed ribbon 321b. Thus, the fixed ribbon 321b is recessed so that the light (the incident light L1) incident on each modulating unit is switched into zero-order light and diffracted light in order other than the zero order (non-zero-order diffracted light).

An amount of recess of the movable ribbon 321a with respect to the fixed ribbon 321b is determined depending on a magnitude of the voltage to be applied to the movable ribbon 321a. In other words, the magnitude of the voltage to be applied by the driver circuit unit 33 is controlled so that a difference between the heights of the movable reflecting surface 322a of the movable ribbon 321a and the fixed reflecting surface 322b of the fixed ribbon 321b is regulated in a plurality of stages. Accordingly, a light amount (the light amount will be hereinafter referred to as an "amount of reflected light") of light (reflected light L2) reflected by the modulating surface 320 of each modulating unit is individually switched in a plurality of gradations depending on the magnitude of the voltage.

In the modulating unit 82, a state of each modulating unit of the spatial light modulator 32 is switched depending on the pattern data under the control of the control portion 9, and at the same time, the light (line beam) emitted from the illuminating optical system 813 is incident on the modulating surface 320 of the spatial light modulator 32 at a determined angle through a mirror 822. However, the line beam is incident on a plurality of modulating units of the spatial light modulator 32 arranged in a line with a long width direction of a linear luminous flux section along the array direction (X-axis direction) of the modulating units. Accordingly, the light emitted from the spatial light modulator 32 is drawing light having a band-shaped section including light modulated spatially corresponding to a plurality of pixels in the sub scanning direction (however, light modulated spatially on a single modulating unit corresponds to a single pixel). Thus, the spatial light modulator 32 receives the light emitted from the light source portion 81 by the modulating surface 320 and performs the spatial modulation depending on the pattern data over the received light.

c. Projecting Optical System 83

The projecting optical system 83 shields the unnecessary light in the drawing light emitted from the spatial light modulator 32 and guides the necessary light to the surface of the substrate W, thereby forming an image of the necessary light on the surface of the substrate W. In other words, the necessary light and the unnecessary light are included in the drawing light emitted from the spatial light modulator 32, and the necessary light advances in a −Z direction along a Z axis and the unnecessary light advances in the −Z direction along an axis which is slightly inclined in a ±X direction from the Z axis. The projecting optical system 83 includes a shielding plate 831 having a through hole formed in the middle to cause only the necessary light to pass, for example, and shields the unnecessary light by the shielding plate 831. In addition to the shielding plate 831, the projecting optical system 83 further includes a shielding plate 832 for shielding ghost light, a plurality of lenses 833 and 834 configuring a zoom portion for increasing (or reducing) a width of the necessary light, a focusing lens 835 for forming an image of the necessary light in a determined magnitude on the substrate W, a driving portion (for example, a motor) (not shown) for driving the focusing lens 835 to change a height position thereof, thereby performing automatic focusing, and the like.

Moreover, the drawing device 1 includes a light amount detector 35 for detecting a light amount of a laser beam reflected by the plurality of modulating units. More specifically, a part of light passing through the projecting optical system 83 is guided to the light amount detector 35 through a half mirror 34 or the like. The light amount detector 35 is configured by a line sensor or the like and is formed to detect the light amount for each of the modulating units. As shown, it is also possible to omit the half mirror 34 and to dispose the light amount detector 35 immediately below the projecting optical system 83, thereby detecting the light passing through the projecting optical system 83 by the light amount detector 35 directly.

Figure 5:
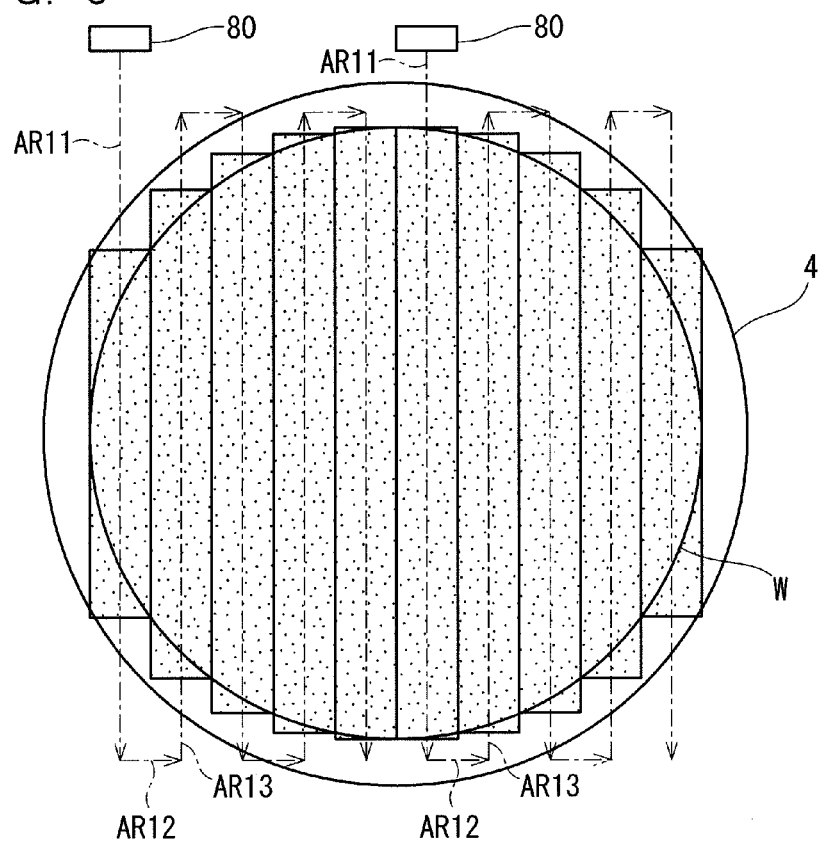
FIG. 5 is a schematic plan view for describing exposure scanning according to the preferred embodiment.

FIG. 5 is a schematic plan view for describing exposure scanning according to the preferred embodiment. In the exposure scanning, the stage driving mechanism 5 moves the stage 4 in an outward direction (which is set to be a +Y direction herein, for example) along a main scanning axis (a Y axis), thereby moving the substrate W with respect to each exposure head 80 relatively along the main scanning axis (outward main scanning). As seen from the substrate W, each exposure head 80 crosses the substrate W in a −Y direction along the main scanning axis as shown by an arrow AR11. Moreover, the drawing light is radiated from each exposure head 80 with start of the outward main scanning. In other words, pattern data (in detail, a portion describing data to be drawn onto a stripe region serving as a drawing target through the outward main scanning in the pattern data) is read and the modulating unit 82 is controlled according to the pattern data. The drawing light subjected to the spatial modulation according to the pattern data is radiated from each exposure head 80 toward the substrate W.

When each exposure head 80 crosses the substrate W once along the main scanning axis while intermittently emitting the drawing light toward the substrate W, a pattern group is drawn on a single stripe region (a region extended along the main scanning axis and causing a width along a sub scanning axis to correspond to a width of the drawing light). Herein, two exposure heads 80 and 80 cross the substrate W at the same time. For this reason, the pattern group is drawn on each of the two stripe regions by one outward main scanning.

When the outward main scanning with the irradiation of the drawing light is ended, the stage driving mechanism 5 moves the stage 4 by a distance corresponding to the width of the drawing light in a predetermined direction (for example, an −X direction) along a sub scanning axis (an X axis). Consequently, the substrate W is moved relatively along the sub scanning axis with respect to each of the exposure heads 80 (sub scanning). As seen from the substrate W, each exposure head 80 is moved by an amount corresponding to the width of the stripe region in a +X direction along the sub scanning axis as shown by an arrow AR12.

When the sub scanning is ended, homeward main scanning with the irradiation of the drawing light is executed. In other words, the stage driving mechanism 5 moves the stage 4 in a homeward direction (herein, the −Y direction) along the main scanning axis (the Y axis). Consequently, the substrate W is moved relatively along the main scanning axis with respect to each exposure head 80 (homeward main scanning). As seen from the substrate W, each exposure head 80 is moved in the +Y direction along the main scanning axis to cross the substrate W as shown by an arrow AR13. On the other hand, when the homeward main scanning is started, the irradiation of the drawing light is started from each exposure head 80. By the homeward main scanning, a pattern group is drawn in a stripe region adjacent to the stripe region drawn by the previous outward main scanning.

When the homeward main scanning with the irradiation of the drawing light is ended, the sub scanning is performed, and furthermore, the outward main scanning with the irradiation of the drawing light is carried out again. By the outward main scanning, a pattern group is drawn on a stripe region adjacent to the stripe region drawn by the previous homeward main scanning Similarly, the main scanning with the irradiation of the drawing light is subsequently performed repetitively with the sub scanning inserted therebetween. When a pattern is drawn in a whole drawing target region, the drawing processing for single pattern data is ended.

<Control Portion 9>

Figure 6:
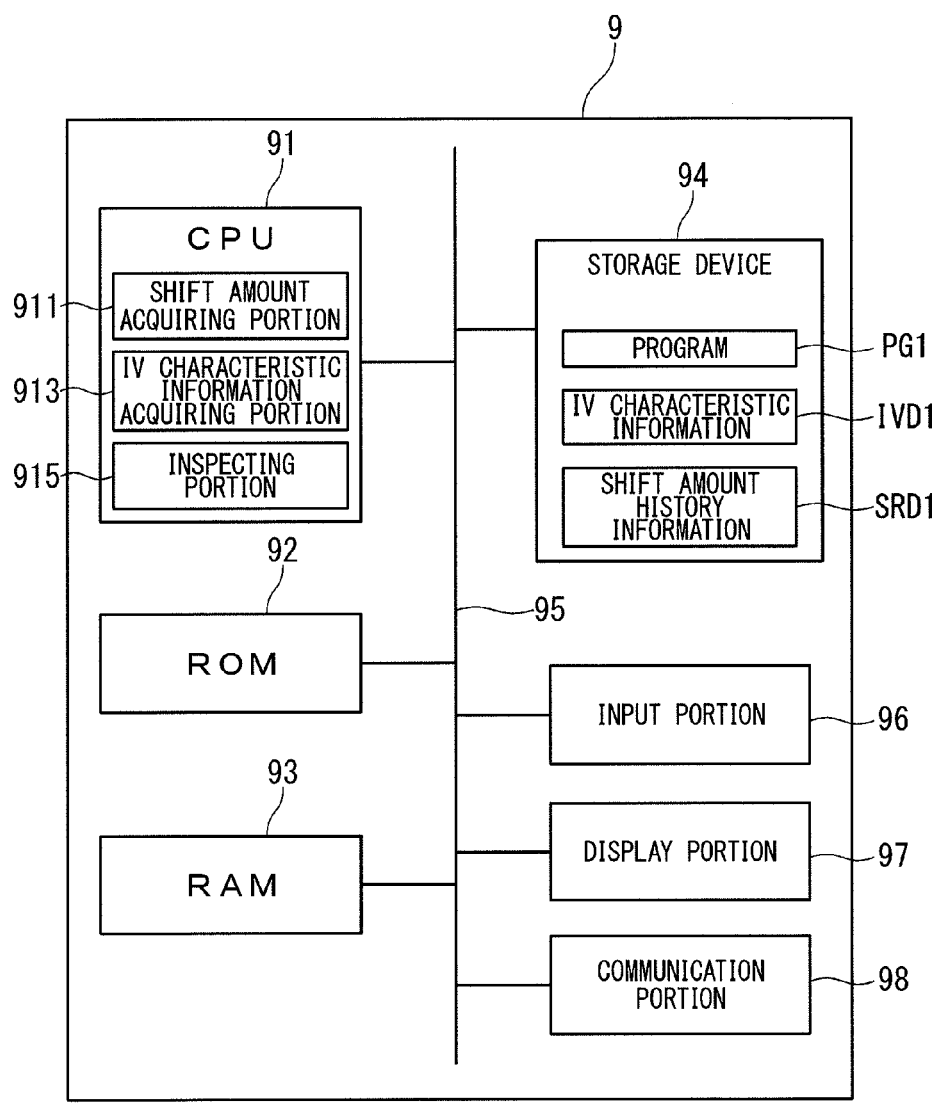
FIG. 6 is a block diagram showing a structure of a control portion according to the preferred embodiment.

FIG. 6 is a block diagram showing a structure of the control portion 9 according to the preferred embodiment. The control portion 9 is connected electrically to each portion provided in the drawing device 1, and controls an operation of each portion of the drawing device 1 while executing various types of calculation processing.

The control portion 9 is configured as a general computer in which a CPU 91, a ROM 92, a RAM 93, a storage device 94 and the like are interconnected through a bus line 95 as shown in FIG. 6, for example. The ROM 92 stores a basic program or the like. The RAM 93 is used as a work area in execution of a predetermined processing by the CPU 91. The storage device 94 is configured by a nonvolatile storage device such as a flash memory or a hard disk device. A program PG1 is installed in the storage device 94. The CPU 91 serving as a main control portion performs calculation processing in accordance with a procedure described in the program PG1 so that various functions (for example, a shift amount acquiring portion 911, an IV characteristic information acquiring portion 913 and an inspecting portion 915) are implemented.

Although the program PG1 is usually prestored in a memory such as the storage device 94 and is thus used, it may be provided in a configuration (a program product) recorded in a recording medium such as a CD-ROM, a DVD-ROM or an external flash memory (or provided by downloading from an external server through a network) and may be stored in a memory such as the storage device 94 additionally or exchangeably. A part or whole of functions may be implemented by the control portion 9 on a hardware basis by a dedicated logic circuit or the like.

In the control portion 9, moreover, an input portion 96, a display portion 97 and a communication portion 98 are also connected to the bus line 95. The input portion 96 is an input device configured by a keyboard and a mouse, for example, and accepts various operations (an operation for inputting a command or various types of data) from an operator. The input portion 96 may be configured by various switches, a touch panel and the like. The display portion 97 is a display device configured by a liquid crystal display, a lamp and the like and displays various information under control of the CPU 91. The communication portion 98 has a data communication function for transmitting/receiving a command, data or the like with an external device through a network.

<2. Operation of Drawing Device>

FIG. 7 is a flowchart showing a flow of processing for acquiring the IV characteristic information of the spatial light modulator 32 to be executed by the drawing device 1 according to the preferred embodiment. A serial operation which will be described below is mainly performed by an operation of the IV characteristic information acquiring portion 913 in accordance with the program PG1. The acquirement of the IV characteristic information is executed in attachment of the spatial light modulator 32 to the drawing device 1, for example.

When the processing for acquiring the IV characteristic information is started, the modulating unit for acquiring the IV characteristic information is first designated (step S10). In step S10, for example, a designating screen for designating one modulating unit or two or more modulating units to acquire the IV characteristic information is displayed on the display portion 97. Then, the operator performs input for designating the modulating unit through the input portion 96 by referring to the screen. In the case where the IV characteristic information for all of the modulating units is acquired, all of the modulating units are designated. In the case where it is empirically expected that a difference between the IV characteristics of the adjacent modulating units is not great, some of the modulating units may be thinned and designated. Moreover, the IV characteristic information acquiring portion 913 may be configured to automatically enable execution of these designating operations.

Subsequently, the IV characteristic, that is, a correspondence relationship between a light amount and a driving value is analyzed for one of the modulating units designated in step S10 (step S11). Then, the IV characteristic information thus acquired is stored in the storage device 94 (step S12). Description will be given to step S11 for analyzing the IV characteristic with reference to FIG. 8.

Figure 8:
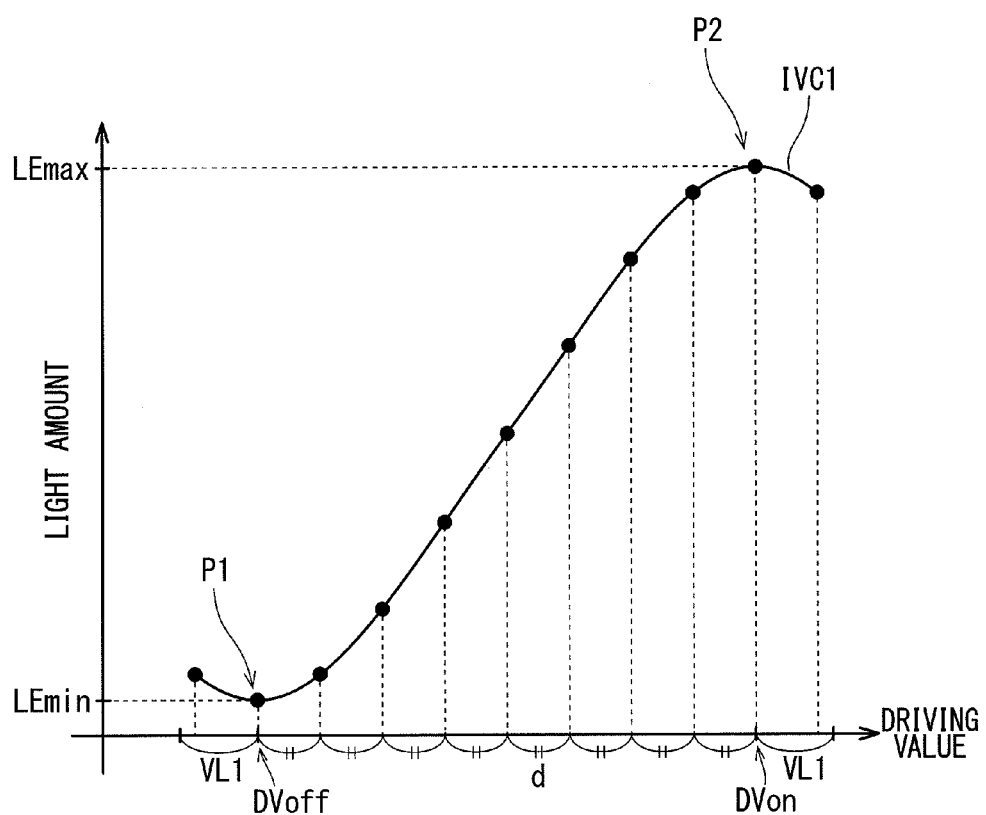
FIG. 8 is a chart showing an IV characteristic of a specific modulating unit in the spatial light modulator.

FIG. 8 is a chart showing an IV characteristic of a specific modulating unit in the spatial light modulator 32. In FIG. 8, a horizontal axis indicates a driving value and a vertical axis indicates a light amount. The driving value is a parameter for controlling the driver circuit unit 33, and corresponds to a voltage to be applied to the movable ribbon 321a of the light modulating element 321 included in each modulating unit of the spatial light modulator 32 by the driver circuit unit 33.

Specifically, the IV characteristic of the modulating unit is analyzed by acquirement of a plurality of driving values which is different from each other and light amounts corresponding to the driving values. As shown in FIG. 8, the light amounts for the respective driving values are plotted onto two-dimensional coordinates and their points are connected to each other so that an IV curve IVC1 is acquired. The IV curve IVC1 is an example of IV characteristic information IVD1 representing a correspondence relationship between a light amount and a voltage (an IV characteristic).

As shown in FIG. 8, the IV curve IVC1 generally has a point P1 where the light amount is minimized (LEmin) and a point P2 where the light amount is maximized (LEmax). In the following, these points P1 and P2 are also referred to as roll over points. Moreover, driving values on the points P1 and P2 are set to be "Voff" and "Von", respectively.

The plurality of driving values in the analysis of the IV characteristic may be selected optionally. For example, in the case where DVon and DVoff as the driving values on the points P1 and P2 are utilized, a plurality of driving values for dividing a portion between the DVon and DVoff at a fixed interval d are specified. In each of the plurality of driving values, it is sufficient to measure the light amount of the reflected light L2 emitted from the modulating unit.

A driving value deviating from a portion between the points P1 and P2 (in the example shown in FIG. 8, a larger driving value than DVon or a smaller driving value than DVoff) may be set to be a driving value for analyzing the IV characteristic. In the case where the movable ribbon 321a is driven with the driving value, however, there is a fear that noncontrollability may be caused due to irreversible deformation of the movable ribbon 321a (snap-down). In order to avoid such a situation, it is desirable to select a measuring voltage from a range obtained by further adding a certain limit value VL1 to both sides of a range from Von to Voff. In other words, in the example of FIG. 8, it is desirable to select the plurality of driving values in a range from Voff−VL1 to Von+VL1.

In step S12 shown in FIG. 7, the IV characteristic information IVD1 representing the IV curve IVC1 is stored in the storage device 94. The IV characteristic information IVD1 may be data recording an approximate expression representing the IV curve IVC1 or data recording the plurality of driving values and the light amounts corresponding to the driving values which correspond to each other on a one-to-one basis, for example.

The IV characteristic information IVD1 thus obtained is referred to when a necessary driving value for obtaining a light amount to be a target is to be determined in an operation for the drawing device 1 to draw a pattern on the substrate W, for example.

Subsequently, it is determined whether IV characteristic information of other modulating units are unnecessary or not (step S13). If the acquirement is unnecessary (YES in step S13), that is, if the IV characteristic information for all of the modulating units set to be targets for acquiring the IV characteristic information is obtained in step S10, the acquirement processing is completed. On the other hand, if there is any modulating unit in which the IV characteristic information has not been acquired (NO in step S13), steps S11 and S12 are executed for the modulating unit in which the IV characteristic information has not been acquired. Thus, the IV characteristic information is acquired for each modulating unit.

As described above, by acquiring the respective IV characteristic information for the respective modulating units, it is possible to manage the correspondence relationship between the light amount and the driving value for each modulating unit. In other words, the driver circuit unit 33 controls each modulating unit based on each piece of IV characteristic information so that a laser beam can be emitted with a modulation into a target light amount value. Consequently, it is possible to appropriately perform pattern drawing in a multi-gradation.

<Inspection Processing of Spatial Light Modulator 32>

Figure 9:
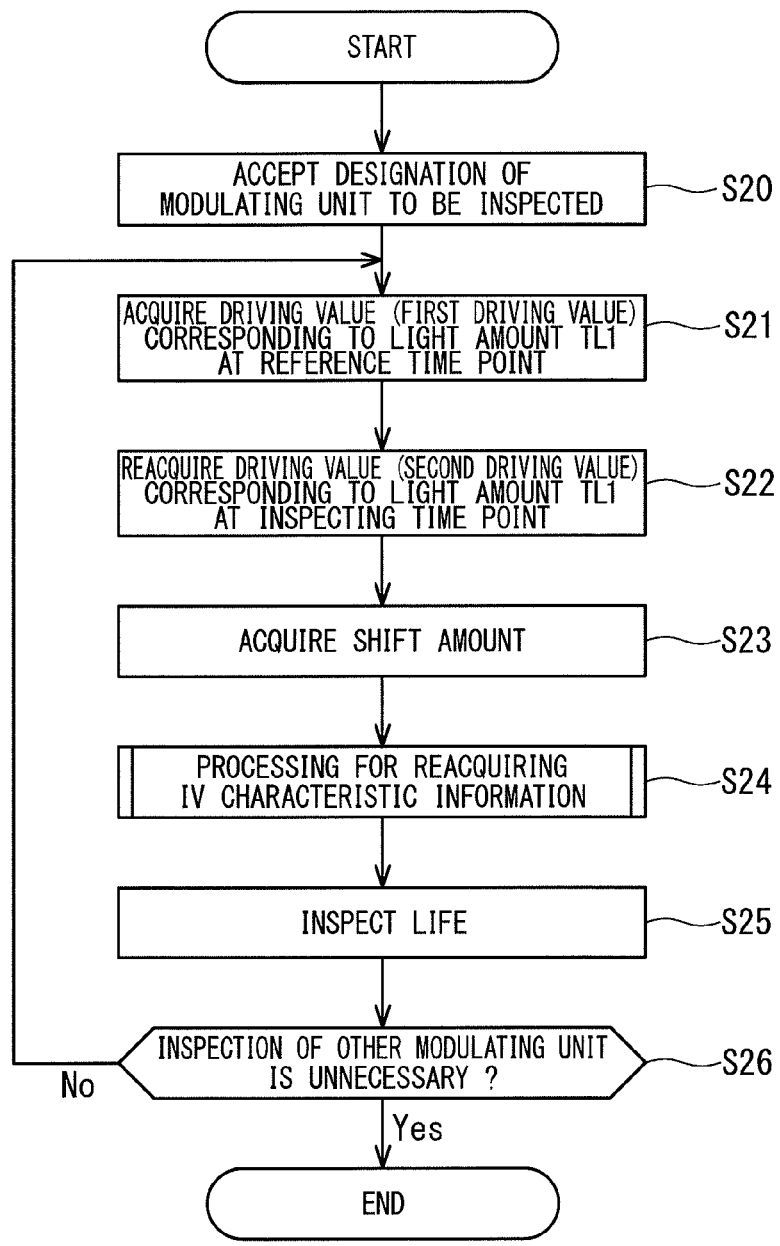
FIG. 9 is a flowchart showing a flow of an inspection of each modulating unit in the spatial light modulator.

FIG. 9 is a flowchart showing a flow for inspecting each modulating unit in the spatial light modulator 32. In the following, in some cases, a time point before execution of the present inspection processing will be referred to as a "reference time point) and a time point at which the present inspection processing is executed will be referred to as an "inspecting time point".

It is known that the modulating surface 320 is deteriorated by oxidation or the like when the spatial light modulator 32 is irradiated with a laser beam. Specifically, it is apparent that the IV characteristic of the modulating unit is changed due to the deterioration in the modulating surface 320. Therefore, there are acquired a driving value at the reference time point and a change amount (a shift amount) of a driving value at the inspecting time point which correspond to a specific light amount value TL1 (step S21 to step S23). In other words, in the present preferred embodiment, a degree of the deterioration in the modulating unit is quantified in a change amount of the driving value. Based on the change amount of the driving value, then, processing for reacquiring the IV characteristic information (step S24) or processing for inspecting a life (step S25) is performed. Each step will be described below in detail.

First of all, the modulating unit for performing the inspection processing is designated (step S20). In step S20, the designating screen for designating one modulating unit or two or more modulating units to be inspected is displayed on the display portion 97, for example. Step S20 is almost the same as step S10 shown in FIG. 7. One or a plurality of modulating units designated herein are inspection processing targets. In the case where the IV characteristic information is acquired for all of the modulating units, all of the modulating units are designated. In the case where it is empirically expected that a difference between the IV characteristics of the adjacent modulating units is not great, some of the modulating units may be thinned and designated. Moreover, the IV characteristic information acquiring portion 913 may be configured to automatically enable execution of these designating operations.

Next, a driving value (a first driving value) corresponding to a specific light amount value TL1 (a first light amount) at the reference time point is acquired (step S21). Subsequently, a driving value (a second driving value) corresponding to the specific light amount value TL1 at the inspecting time point is reacquired (step S22). Then, a differential value between the driving value at the reference time point and the driving value at the inspecting time point corresponding to the specific light amount value TL1 is acquired as a shift amount (step S23). The processing of step S21 to step S23 is mainly executed by an operation of the shift amount acquiring portion 911 in accordance with the program PG1.

Thereafter, the processing for reacquiring the IV characteristic information is executed (step S24). In step S24, the IV characteristic information (second IV characteristic information) at the inspecting time point is acquired based on the IV characteristic information (first IV characteristic information) acquired at the reference time point and the shift amount acquired in step S13. The processing of step S24 is mainly executed by an operation of the IV characteristic information acquiring portion 913 in accordance with the program PG1.

Figure 10:
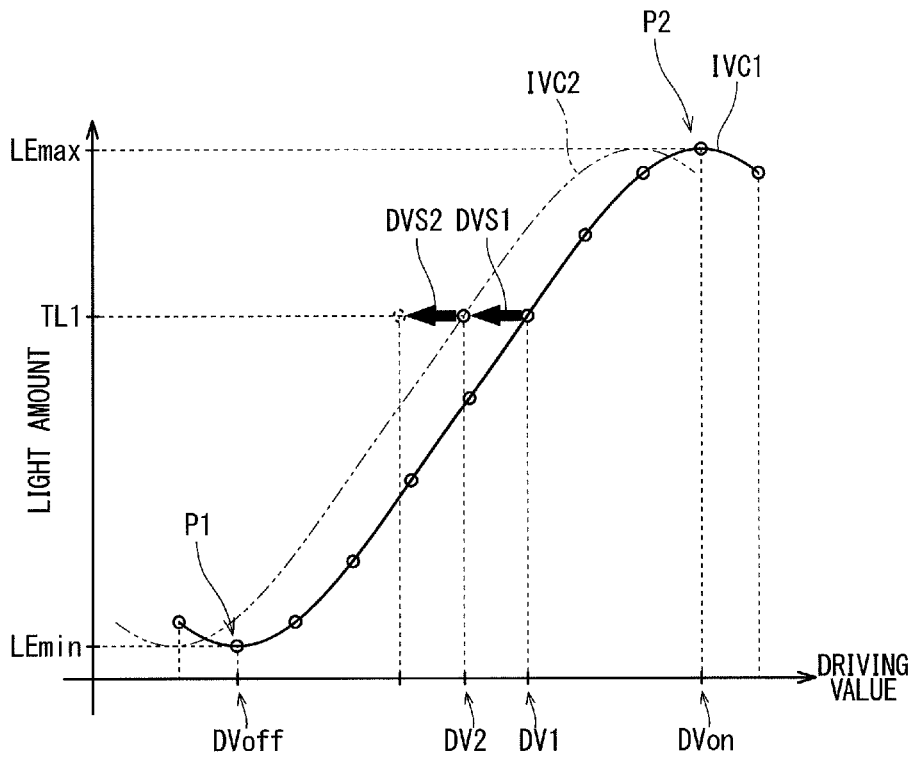
FIG. 10 is a chart for describing a change in the IV characteristic caused by deterioration in regard to the specific modulating unit in the spatial light modulator.

Herein, the processing of step S21 to step S24 shown in FIG. 9 will be specifically described. FIG. 10 is a chart for describing a change in the IV characteristic due to deterioration for the specific modulating unit in the spatial light modulator 32. In FIG. 10, a horizontal axis indicates a driving value and a vertical axis indicates a light amount.

In the following description, a time point at which the IV curve IVC1 shown in FIG. 8 is acquired is set to be a reference time point and it is assumed that processing for inspecting a deterioration situation is performed after an operating time passes to some degree from the reference time point. The IV curve IVC1 shown in FIG. 10 is identical to the IV curve IVC1 shown in FIG. 8.

First of all, in step S21, the shift amount acquiring portion 911 acquires a driving value corresponding to a specific light amount at the reference time point. As shown in FIG. 10, according to the IV curve IVC1 at the reference time point, the driving value corresponding to the specific light amount value TL1 is represented as DV1. For this reason, the shift amount acquiring portion 911 acquires the driving value DV1 as the first driving value. The IV curve IVC1 is stored as the IV characteristic information IVD1 in the storage device 94. In other words, the IV characteristic information IVD1 is an example of information indicative of the first driving value (DV1).

In step S22, subsequently, the shift amount acquiring portion 911 acquires the second driving value corresponding to the specific light amount value TL1 at the inspecting time point. A method of acquiring the second driving value will be described with reference to FIG. 11.

Figure 11:
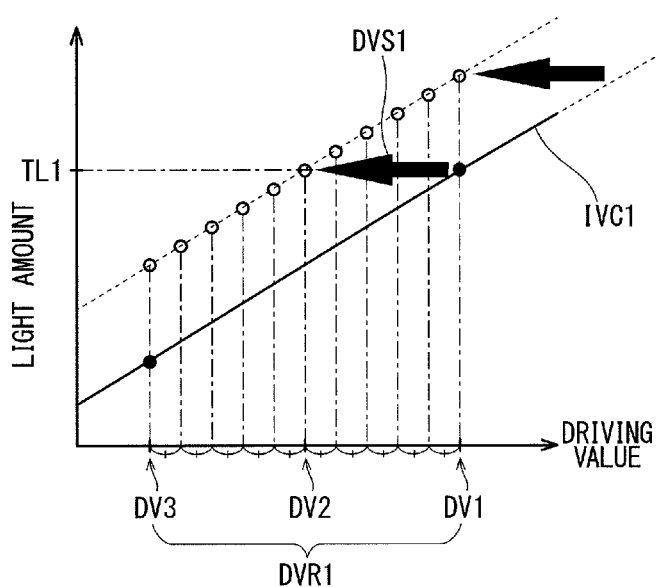
FIG. 11 is a chart for describing a method of acquiring a second driving value corresponding to a specific light amount value.

FIG. 11 is a chart for describing the method of acquiring the second driving value corresponding to the specific light amount value TL1. In FIG. 11, a horizontal axis indicates a driving value and a vertical axis indicates a light amount.

In the example shown in FIG. 11, the IV characteristic of each modulating unit is shifted in a negative direction of an axis related to the driving value due to deterioration in the surface of the light modulating element 321. The shift amount acquiring portion 911 selects a plurality of driving values within a range DVR1 between the first driving value DV1 and a driving value DV3 (a third driving value) smaller than the first driving value DV1. Then, the shift amount acquiring portion 911 gives the driving values to the driver circuit unit 33 to drive the modulating units to be inspected. Consequently, the light amount value of each of the driving values is measured. In the case where a direction in which the driving value is shifted due to the deterioration is a positive direction, it is sufficient that the driving value DV3 is set to be larger than DV1.

In the graph shown in FIG. 11, referring to each of the plurality of driving values obtained by dividing a range from DV1 as the first driving value to DV3 as the third driving value into ten equal parts, a corresponding light amount value is acquired and plotted onto two-dimensional coordinates. The shift amount acquiring portion 911 is configured to acquire, as the second driving value, a driving value corresponding to a light amount which is coincident with the specific light amount value TL1 based on a plurality of light amount values acquired by measurement. If there is no light amount value which is coincident with the specific light amount value TL1 in results of the measurement of the light amount values, a driving value corresponding to the light amount value closest to the specific light amount value TL1 may be set to be the second driving value. Moreover, a relational expression may be obtained based on a correspondence relationship between the driving value and the light amount value acquired by the measurement to obtain the driving value corresponding to the specific light amount value TL1 in accordance with the relational expression. It is sufficient that the relational expression is set to be a polynomial expression in order of one or more in which the driving value is a variable, for example. If a difference between the first driving value DV1 and the third driving value DV3 is sufficiently small as shown in FIG. 11, the relational expression of the light amount value and the driving value may be set to be a linear expression in which the driving value is a variable.

In step S23, the shift amount acquiring portion 911 performs subtraction processing over the first driving value (=DV1) and the second driving value (=DV2) obtained in steps S21 and S22, thereby acquiring DVS1 (=DV1−DV2) that is a differential value as a shift amount. The shift amount acquiring portion 911 stores the shift amount thus acquired in the storage device 94 (or the RAM 93).

The shift amount is data which specifically indicates a degree of deterioration in a corresponding modulating unit. For this reason, by accumulating the shift amount, it is possible to appropriately manage the degree of the deterioration from a using start time point of the corresponding modulating unit, for example. Therefore, the storage device 94 stores, as shift amount history information SRD1, a shift amount acquired in the previous inspection processing together with the shift amount obtained in the present inspection processing for each modulating unit (see FIG. 6).

FIG. 12 is a flowchart showing a detailed flow of the processing for reacquiring the IV characteristic information. First of all, the IV characteristic information acquiring portion 913 determines whether the IV characteristic information is to be reacquired for the modulating unit having the shift amount acquired in step S23 (step S31). In step S31, the modulating unit having the shift amount acquired may be set to always reacquire the IV characteristic information or may be set to reacquire the IV characteristic information when the shift amount exceeds a predetermined threshold. Moreover, it may be also considered to set in advance that the IV characteristic information is not to be acquired.

If the IV characteristic information is reacquired (YES in step S31), step S32 is executed. If the IV characteristic information is not reacquired (NO in step S31), the processing for reacquiring the IV characteristic information in step S24 is ended.

In step S32, the IV characteristic information acquiring portion 913 determines whether the IV characteristic information can be acquired simply or not (step S32). Specifically, the IV characteristic information acquiring portion 913 accumulates the shift amount recorded in the shift amount history information SRD1 to obtain an accumulated shift amount. As described in step S11, it is assumed that the shift amount to be accumulated is recorded after the last time point at which the correspondence relationship between the light amount value and the driving value is analyzed (for example, a time point at which the IV curve IVC1 is obtained).

Then, the IV characteristic information acquiring portion 913 compares the accumulated shift amount with the prescribed threshold, thereby determining necessity of the acquirement of the IV characteristic information. The threshold is prestored in the storage device 94 or the like, and it may be read appropriately or may be set appropriately by an operator.

For example, as shown in FIG. 10, the shift amount DVS1 is generated at the last reference time point at which the IV curve IVC1 is obtained at a current inspecting time point in the modulating unit to be the inspecting target. For this reason, the accumulated shift amount at and after the time point at which the IV curve IVC1 is acquired is equivalent to DVS1. If a shift amount DVS2 is further generated in a next inspection, the accumulated shift amount is equivalent to a value (DVS1+DVS2) obtained by adding DVS2 to DVS1. In the next inspection, accordingly, it is determined whether the accumulated shift amount exceeds the prescribed threshold or not in step S33.

If the accumulated shift amount does not exceed the prescribed threshold (YES in step S32), the IV characteristic information is acquired by a simple method (step S33). The simple method is specifically as follows. Specifically, as shown in FIG. 10, the IV curve IVC1 at the reference time point (in other words, the IV characteristic information at a time point at which the accumulated shift amount is zero) is moved in parallel in an axial direction related to the driving value, that is, a direction in which the driving value corresponding to the specific light amount value LT1 is shifted (herein, a negative direction) by an amount corresponding to the accumulated shift amount (herein, DVS1). Consequently, the IV characteristic information acquiring portion 913 acquires the IV curve IVC2 shown in a two-dot chain line. The IV curve IVC2 is equivalent to the second IV characteristic information.

The IV curve IVC2 is not strictly the IV characteristic information itself at the inspecting time point. However, the shift of the driving value may be caused by deterioration to the same degree in each light amount other than the specific light amount value TL1. For this reason, it is possible to approximate the IV characteristic of the specific modulating unit at the inspecting time point by the IV curve IVC2 obtained by moving the IV curve IVC1 by an amount corresponding to the shift amount DVS1.

On the other hand, if the accumulated shift amount exceeds the prescribed threshold (NO in step S32), the IV characteristic information is reacquired, not by the simple method, but by reanalysis of the correspondence relationship between the light amount and the driving value (step S34). Since the step S34 can be executed in almost the same procedure as step S11 shown in FIG. 7, detailed description will be omitted.

If the accumulated shift amount is large to some degree, it is namely estimated that the degree of the deterioration is high. There is a fear that the IV curve shifted uniformly may be greatly different from an actual IV curve as described above. Therefore, if the accumulated shift amount exceeds the prescribed threshold, the correspondence relationship between the light amount and the driving value is reanalyzed so that accurate IV characteristic information is acquired.

As described above, in the case of the simple method, the IV characteristic information can be acquired much more easily as compared with the case where the correspondence relationship between the light amount and the driving value is reanalyzed. For this reason, the IV characteristic information can be reacquired efficiently. Particularly, in the case where the IV characteristic information is to be reacquired for all of the modulating units, it is possible to considerably shorten a time by utilizing the shift amount of the driving value. Consequently, it is possible to effectively reduce a time required for stopping a manufacturing line in which the drawing device 1 is incorporated, for example.

In step S33 or step S34, the reacquired IV characteristic information is restored in the storage device 94 (step S35). Subsequently, control of a light amount of a relevant modulating unit is executed based on the IV characteristic information stored newly in step S35. As described above, the processing for reacquiring the IV characteristic information is completed.

Returning to FIG. 9, when the processing for reacquiring the IV characteristic information (step S24) is completed, the inspecting portion 915 subsequently inspects the life of the modulating unit (step S25). Specifically, it is determined whether a service life is reached or not based on the shift amount recorded in the shift amount history information SRD1.

Specifically, if the accumulated shift amount of the driving value corresponding to the specific light amount value TL1 which is accumulated at a time point at which the use of the spatial light modulator 32 is started exceeds a preset threshold as the service life of the modulating unit, for example, it is determined that the service life is reached. A threshold for executing maintenance may be preset to the spatial light modulator 32 and the inspecting portion 915 may determine whether the accumulated shift amount exceeds the threshold or not. The operator is appropriately notified of a result of the decision (a result of the inspection) obtained by the inspecting portion 915 through an output device such as a speaker, a display or a lamp. Consequently, the operator can grasp which modulating unit is deteriorated. As a result, the operator can suitably suppress occurrence of a drawing failure in the drawing device 1 by setting the drawing device 1 so as to execute the drawing processing without using the modulating unit.

Subsequently, it is determined whether the inspection is unnecessary for the other modulating units or not (step S26). If the inspection is unnecessary (YES in step S26), that is, if the inspection is completed for all of the modulating units set to be the inspecting targets in step S20, the inspection processing is ended. On the other hand, if there is an uninspected modulating unit (NO in step S26), step S21 to step S25 are executed for the uninspected modulating unit. Thus, the inspection is sequentially performed for each modulating unit.

Although the preferred embodiment has been described above, the present invention is not limited thereto and may be variously changed.

For example, the drawing device 1 does not need to be configured to enable execution of both the processing for acquiring the IV characteristic information shown in FIG. 7 and the detection processing shown in FIG. 10, and may be configured to enable execution of only at least one of the pieces of processing.

Moreover, each of the pieces of processing shown in FIGS. 7 and 10 is performed with the spatial light modulator 32 incorporated in the drawing device 1. However, in the inspecting device configured to enable the execution of the respective pieces of processing shown in FIGS. 7 and 10, the spatial light modulator 32 removed from the drawing device 1 may be inspected. It is sufficient that the inspecting device includes, at a minimum, any of the components of the drawing device 1 which are used in the pieces of processing of FIGS. 7 and 10 (for example, the light source portion 81, the driver circuit unit 33, the light amount detector 35, the shift amount acquiring portion 911, the IV characteristic information acquiring portion 913 and the inspecting portion 915).

While the invention has been shown and described in detail, the foregoing description is in all aspects illustrative and not restrictive. It is therefore understood that numerous modifications and variations can be devised without departing from the scope of the invention.

What is claimed is:

1. An inspecting device for inspecting a spatial light modulator to modulate a light amount while reflecting an incident laser beam for every plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from said base surface, the inspecting device comprising:

a modulator driving portion for applying a voltage corresponding to a driving value to each of said plurality of modulating units to drive said movable ribbon, to control a light amount of a laser beam output by said modulating unit;

a light amount detector for detecting the light amount of said laser beam reflected by each of said plurality of modulating units;

a storing portion for storing information indicative of a first driving value corresponding to a first light amount for one of said plurality of modulating units or for every two or more of said modulating units; and a shift amount acquiring portion for acquiring a second driving value corresponding to an output of said first light amount again, to acquire a differential value between said first driving value and said second driving value as a shift amount for one of said plurality of modulating units or for every two or more of said modulating units.

2. The inspecting device according to claim 1, wherein said storing portion stores information indicative of a correspondence relationship between a light amount and a driving value for one of said plurality of modulating units or for every two or more of said modulating units, the information being first IV characteristic information in which a driving value corresponding to the output of said first light amount is set to be said first driving value, said inspecting device further comprising:

an IV characteristic information acquiring portion for changing a driving value corresponding to each light amount indicated by said first IV characteristic information by an amount corresponding to said shift amount, to acquire second IV characteristic information for one of said plurality of modulating units or for every two or more of said modulating units.

3. The inspecting device according to claim 2, wherein said first IV characteristic information is information indicative of a first IV curve representing a correspondence relationship between a driving value and a light amount on two-dimensional coordinates constituted by an axis of the driving value and an axis of the light amount, and said IV characteristic information acquiring portion acquires, as said second IV characteristic information, a second IV curve obtained by moving said first IV curve by an amount corresponding to said shift amount along the axis of said driving value.

4. The inspecting device according to claim 2, wherein said storing portion stores, as shift amount history information, said shift amount which has been acquired by said shift amount acquiring portion for one of said plurality of modulating units or for every two or more of said modulating units, and said IV characteristic information acquiring portion determines necessity of acquirement of said second IV characteristic information based on an accumulated shift amount in which said shift amount recorded in said shift amount history information is accumulated.

5. The inspecting device according to claim 1, wherein said shift amount acquiring portion acquires said second driving value corresponding to said first light amount based on a relationship between a plurality of driving values included in a range from said first driving value to a third driving value and a light amount corresponding to each of the plurality of driving values.

6. The inspecting device according to claim 1, further comprising:

an inspecting portion for performing an inspection for one of said plurality of modulating units or for every two or more of said modulating units, wherein said storing portion stores, as shift amount history information, said shift amount which has been acquired by said shift amount acquiring portion for one of said plurality of modulating units or for every two or more of said modulating units, and said inspecting portion inspects said modulating unit based on said shift amount history information.

7. The inspecting device according to claim 6, wherein said inspecting portion performs an inspection for comparing an accumulated shift amount in which said shift amount recorded in said shift amount history information is accumulated with a prescribed threshold indicative of a life of said modulating unit.

8. A drawing device for drawing a pattern on a substrate, the drawing device comprising:
   a spatial light modulator for modulating a light amount while reflecting an incident laser beam for every plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from said base surface;
   a modulator driving portion for applying a voltage corresponding to a driving value to each of said plurality of modulating units to drive said movable ribbon, to control a light amount of a laser beam output by said modulating unit;
   a light amount detector for detecting the light amount of said laser beam reflected by each of said plurality of modulating units;
   a storing portion for storing information indicative of a first driving value corresponding to a first light amount for one of said plurality of modulating units or for every two or more of said modulating units; and
   a shift amount acquiring portion for acquiring a second driving value corresponding to an output of said first light amount again, to acquire a differential value between said first driving value and said second driving value as a shift amount for one of said plurality of modulating units or for every two or more of said modulating units.

9. A method of inspecting a spatial light modulator for modulating a light amount while reflecting an incident laser beam by application of a voltage corresponding to a driving value from a modulator driving portion through each of a plurality of modulating units being arranged in a predetermined direction, the plurality of modulating units each including at least one light modulating element including a fixed ribbon having a fixed reflecting surface with a constant height from a base surface and a movable ribbon having a movable reflecting surface with a variable height from said base surface, the method comprising the steps of:
   (a) acquiring a first driving value corresponding to a first light amount of said laser beam reflected by said modulating unit for one of said plurality of modulating units or for every two or more of said modulating units;
   (b) acquiring a second driving value corresponding to said first light amount again for one of said modulating units or for every two or more of said modulating units; and
   (c) acquiring a differential value between said first driving value and said second driving value as a shift amount.

10. The inspecting method according to claim 9, further comprising the steps of:
   (d) storing, in a storing portion, information indicative of a correspondence relationship between a light amount and a driving value for one of said plurality of modulating units or for every two or more of said modulating units, the information being first IV characteristic information in which a driving value corresponding to the output of said first light amount is set to be said first driving value; and
   (e) changing a driving value corresponding to each light amount indicated by said first IV characteristic information by an amount corresponding to said shift amount, to acquire second IV characteristic information for one of said plurality of modulating units or for every two or more of said modulating units.

11. The inspecting method according to claim 10, wherein said first IV characteristic information is information indicative of a first IV curve representing a correspondence relationship between a driving value and a light amount on two-dimensional coordinates constituted by an axis of the driving value and an axis of the light amount, and
   said step (e) includes a step of acquiring, as said second IV characteristic information, a second IV curve obtained by moving said first IV curve by an amount corresponding to said shift amount along the axis of said driving value.

12. The inspecting method according to claim 10, further comprising the step of:
   (f) storing, as shift amount history information, said shift amount which has been acquired by said shift amount acquiring portion for one of said plurality of modulating units or for every two or more of said modulating units,
   wherein said step (e) includes a step of determining necessity of acquirement of said second IV characteristic information based on an accumulated shift amount in which said shift amount recorded in said shift amount history information is accumulated.

13. The inspecting method according to claim 9, wherein said step (c) includes a step of acquiring said second driving value corresponding to said first light amount based on a relationship between a plurality of driving values included in a range from said first driving value to a third driving value and a light amount corresponding to each of the plurality of driving values.

14. The inspecting method according to claim 9, further comprising the steps of:
   (g) storing said shift amount acquired in said step (c) as shift amount history information in the storing portion for one of said plurality of modulating units or for every two or more of said modulating units, and
   (h) performing an inspection based on said shift amount history information for one of said plurality of modulating units or for every two or more of said modulating units.

15. The inspecting method according to claim 14, wherein said step (h) includes a step of performing an inspection for comparing an accumulated shift amount in which said shift amount recorded in said shift amount history information is accumulated with a prescribed threshold indicative of a life of said modulating unit.

* * * * *